(12) United States Patent
Baroud et al.

(10) Patent No.: US 9,133,009 B2
(45) Date of Patent: Sep. 15, 2015

(54) DEVICE FOR FORMING DROPS IN A MICROFLUIDIC CIRCUIT

(75) Inventors: Charles Baroud, Paris (FR); Rémi Dangla, Paris (FR)

(73) Assignees: CENTRE NATIONAL DE LA RECHERCHE SCIENTIFIQUE, Paris (FR); ECOLE POLYTECHNIQUE, Palaiseau Cedex (FR)

( * ) Notice: Subject to any disclaimer, the term of this patent is extended or adjusted under 35 U.S.C. 154(b) by 209 days.

(21) Appl. No.: 13/637,779

(22) PCT Filed: Mar. 28, 2011

(86) PCT No.: PCT/FR2011/050677
§ 371 (c)(1),
(2), (4) Date: Dec. 10, 2012

(87) PCT Pub. No.: WO2011/121220
PCT Pub. Date: Oct. 6, 2011

(65) Prior Publication Data
US 2013/0078164 A1    Mar. 28, 2013

(30) Foreign Application Priority Data

Mar. 30, 2010    (FR) ..................... 10 01298

(51) Int. Cl.
*B01L 3/00* (2006.01)
*B01F 15/02* (2006.01)
(Continued)

(52) U.S. Cl.
CPC ............. *B67D 3/0058* (2013.01); *B01L 3/0241* (2013.01); *B01L 3/502784* (2013.01); *B01F 13/0062* (2013.01); *B01F 13/04* (2013.01); *B01F 15/02* (2013.01); *B01L 2200/0673* (2013.01); *B01L 2300/0816* (2013.01); *B01L 2400/0487* (2013.01); *C12N 11/04* (2013.01); *G01N 35/08* (2013.01)

(58) Field of Classification Search
None
See application file for complete search history.

(56) References Cited

U.S. PATENT DOCUMENTS

2003/0054558 A1*  3/2003  Kurabayashi et al. .......... 436/63
2006/0051329 A1*  3/2006  Lee et al. ..................... 424/93.7
(Continued)

FOREIGN PATENT DOCUMENTS

CN        101484229           7/2009
WO     WO 2007/133710 A2    11/2007
(Continued)

OTHER PUBLICATIONS

International Search Report and Written Opinion from International Application No. PCT/FR2011/050677, mailed Jun. 27, 2011.
(Continued)

*Primary Examiner* — Jennifer Wecker
(74) *Attorney, Agent, or Firm* — Alston & Bird LLP

(57) ABSTRACT

The invention relates to a device (1) for forming droplets in a microfluidic circuit, the device comprising a chamber (3) containing a first fluid and defined by two opposite walls (10, 11) that diverge relative to each other in at least one given direction, and a microchannel (8) containing a second fluid and leading into a zone of said chamber (3) that is upstream relative to the given direction, the outlet of the microchannel (8) into the chamber (3) constituting an enlargement in the flow section for the second fluid, and the enlargement giving rise to droplets (14) of the second fluid forming within the first fluid.

28 Claims, 3 Drawing Sheets

(51) Int. Cl.
*F15C 1/04* (2006.01)
*B01J 14/00* (2006.01)
*B67D 3/00* (2006.01)
*B01L 3/02* (2006.01)
*A61M 37/00* (2006.01)
*B01J 13/00* (2006.01)
*G01N 35/08* (2006.01)
*C12N 11/04* (2006.01)
*B01F 13/04* (2006.01)
*B01F 13/00* (2006.01)

(56) References Cited

U.S. PATENT DOCUMENTS

| | | | |
|---|---|---|---|
| 2009/0098168 A1* | 4/2009 | Hettiarachchi et al. | 424/400 |
| 2009/0197977 A1* | 8/2009 | Haeberle et al. | 516/10 |
| 2009/0283148 A1* | 11/2009 | Shinoda et al. | 137/2 |
| 2010/0184928 A1* | 7/2010 | Kumacheva | 526/65 |
| 2010/0188466 A1* | 7/2010 | Clarke | 347/75 |
| 2011/0218123 A1* | 9/2011 | Weitz et al. | 506/27 |
| 2011/0223314 A1* | 9/2011 | Zhang et al. | 427/2.1 |
| 2012/0075389 A1* | 3/2012 | Clarke et al. | 347/73 |
| 2012/0222748 A1* | 9/2012 | Weitz et al. | 137/1 |

FOREIGN PATENT DOCUMENTS

| | | |
|---|---|---|
| WO | WO 2009/004314 | 1/2009 |
| WO | WO 2009/048532 A2 | 4/2009 |
| WO | WO 2010/033200 A2 | 3/2010 |

OTHER PUBLICATIONS

Yung-Chieh Tan et al.; "Controlled Microfluidic Encapsulation of Cells, Proteins, and Microbeads in Lipid Vesicles"; Journal of the American Chemical Society, US; vol. 128, No. 17; Apr. 5, 2006; pp. 5656-5658; XP002530562.

Cordero M-L et al.; "Holographic Control of Droplet Microfluidics"; Proceedings of the Spie, Spie, Bellingham, VA, US; vol. 7038, Aug. 10, 2008; pp. 70381J-1; XP007910334.

Michele Zagnoni, E.A.; "Electrically Initiated Upstream Coalescence Cascade of Droplets in a Mircofluidic Flow"; Physical Review E; vol. 8, No. 4; Oct. 2009; pp. 046303-1-046303-9; XP002611761.

Cordero, Maria Luisa, et al.; "Thermocapillary Manipulation of Droplets Using Holographic Beam Shaping: Microfluidic Pin Ball"; Applied Physics Letters, AIP, American Institute of Physics, Melville, NY, US; vol. 93, No. 4; Jul. 24, 2008; pp. 34107-34107; XP012113187.

Office Action from related Chinese Appl. No. 201180017345.2, dated Oct. 10, 2014.

Office Action from related Japanese Appl. No. 2013-501905, dated Dec. 2, 2014.

* cited by examiner

DEVICE FOR FORMING DROPS IN A MICROFLUIDIC CIRCUIT

FIELD

The present invention relates to a device for forming droplets in a microfluidic circuit, in particular microdroplets and nanodroplets of size that lies in the range a few hundreds of nanometers to a few hundreds of micrometers.

BACKGROUND

Such droplets are used in several technical fields. In each field, the methods of forming droplets are different.

A first technical field relates to on-chip laboratory applications or other biotechnologies. In this field, a first approach consists in using a device having at least one microchannel in which a first fluid flows, also known as a "carrier" fluid, which microchannel leads perpendicularly into at least one second microchannel in which a second fluid flows that is not miscible with the first fluid. The first fluid (generally oil) shears the second fluid (generally water in biological applications) so as to form droplets of the second fluid, which droplets are then transported by the first fluid. The flow rates of the two fluids and the shapes of the microchannels are adjusted so as to form droplets of a desired size at a desired rate, where size and rate also depend on the viscosities of the two fluids.

Devices of that type necessarily include forcing means such as a pump to cause the two fluids to flow. Since droplet size is a function of the flow rate of each fluid, it is necessary to adjust the fluid flow rates accurately, thereby making such devices difficult to use.

For example, document US 2006/0051329 describes a device for encapsulating droplets containing cells, the device having both a first channel for delivering a flow of fluid containing the cells, which channel presents a flare in its downstream portion (see FIG. 9), and also a second channel conveying a flow of oil that crosses the first channel perpendicularly, the oil flow shearing the flow of fluid containing the cells so as to form droplets. A similar device is described in the document "Controlled microfluidic encapsulation of cells, proteins, and microbeads in lipid vesicles", by Yung-Chieh Tan et al., Journal of the American Chemical Society, Vol. 128, No. 17, Apr. 5, 2006, pp. 5656-5658.

Document WO 2009/048532 also describes a device for forming droplets, which device comprises a first channel for delivering gas into which two opposite side channels lead to deliver water in such a manner as to form bubbles of gas surrounded by water, and in which two other side channels lead to deliver oil enabling the bubbles to be encapsulated. The bubbles are formed by shearing a flow of a first fluid (gas) with the help of a flow of another fluid (water).

Other devices for forming droplets by shearing a fluid flow are disclosed by the following documents: WO 2010/033200; WO 2007/133710; "Holographic control of droplet microfluidics", by M-L Cordero et al., Proceedings of the SPIE, Vol. 7038, Aug. 10, 2008, pp. 70381J-1; "Electrically initiated upstream coalescence cascade of droplets in a microfluidic flow", by Michele Zagnoni, et al., Physical Review E., Vol. 80, No. 4, October 2009, pp. 046303-1-046303-9; and "Thermocapillary manipulation of droplets using holographic beam shaping: microfluidic pin ball", by M-L Cordero et al., Applied Physics Letters, Vol. 93, No. 3, Jul. 24, 2008, p. 34107.

Document US 2009/0098168 discloses a device for forming droplets, which device has a channel for delivering a fluid flow that leads into an expansion nozzle via an orifice. The nozzle has two diverging walls and contains a fluid that is different from the fluid flowing in the channel upstream from the orifice. Droplets are formed because of hydrodynamic pinching at the orifice, while the diverging walls ensure that the emulsion is uniform. The system forces a central stream of a dispersed phase and two side sheath flows through the orifice into a second chamber, with the convergence of the flow surrounding the liquid serving to fraction the thread at the orifice.

A second approach is that of so-called "digital" microfluidics, in which the droplets are typically formed by electrowetting, by applying different electrical voltages to different portions of the droplets.

Droplets formed using that technique are of a size that is much greater than that of nanodroplets or microdroplets. That technique also raises the problem of contamination between droplets and of droplet evaporation.

Finally, there exist several approaches for producing droplets on demand by quickly ejecting liquid through a needle or a hole with the help of devices that are often similar to ink jet printer systems, producing droplets that impact against a surface with high energy and generate splashes. Those devices further require expensive technical means such as high voltage sources or precision motors.

A second technical field relates to materials science, in which several approaches have been developed in order to produce foams or emulsions, and thus populations of bubbles or droplets. Applications are varied and relate in particular to the food industry and the cosmetics industry.

Other approaches consist in encapsulating droplets in other droplets. For example, a water droplet may be encapsulated in an oil droplet, which is itself contained in water. All of those approaches require the use of expensive forcing means that are difficult to implement.

In addition, and in general, it is desired to increase the rates at which droplets are produced while guaranteeing that droplets or bubbles are obtained in monodisperse form, i.e. presenting size that is constant and controlled.

SUMMARY

A particular object of the invention is to provide a solution to those problems that is simple, effective, and inexpensive.

To this end, the invention provides a device for forming droplets in a microfluidic circuit, the device being characterized in that it comprises a chamber containing a first fluid and defined by two opposite walls that diverge relative to each other in at least one given direction, and a microchannel that contains a second fluid and that leads into a zone of said chamber that is upstream relative to the given direction, the outlet of the microchannel into the chamber including an increase in the flow section for the second fluid, with this increase giving rise to droplets of the second fluid being formed and being detached from the second fluid contained in the microchannel.

In that device, the second fluid at the outlet from the microchannel into the chamber is subjected to two opposing forces due to surface tension. A first force is a surface energy gradient that is due to the change in the surface area of the droplet as it forms, and that tends to extract the second fluid from the microchannel so as to form a "finger" of the second fluid projecting into the chamber and connected to the second fluid contained in the microchannel, and then to form a droplet by separating the finger from the second fluid contained in the microchannel.

A second force acting in the direction opposite to the first force and corresponding to capillary force tends to hold the finger of the second fluid attached to the second fluid contained in the microchannel.

The above-mentioned finger is detached from the second fluid contained in the microchannel when the first force becomes greater than the second force. For a given shape of the microchannel and of the chamber, the first force is a function in particular of the volume of the finger of second fluid. Thus, in operation, the volume of the finger increases progressively until the first force becomes greater than the second force and the second finger becomes detached so as to form a droplet.

The droplet is then transported from upstream to downstream by the increase in the section of the chamber.

It should be observed that there is no need for the first and second fluids to be flowing, the important point is merely that the second fluid is delivered to the outlet of the microchannel into the chamber. There is therefore no need to provide means for forcing the various fluids. The transport of droplets of the second fluid within the chamber results from the increase in the flow section. A droplet situated in a zone of small section, in which it has a flattened shape, is naturally attracted by a zone of larger section in which it can take up a shape that is more spherical.

Furthermore, the size of the droplets is substantially independent of the flow rate of the second fluid. It is essentially a function of the second fluid delivery section at the inlet to the chamber and of the divergence of said opposite walls of the chamber, i.e. it is a function of geometrical parameters that are fixed and do not vary over time, the size of the droplets thus being calibrated accurately.

Furthermore, droplet size does not depend on surface tension, since the same surface tension acts both to detach the droplets and to retain them. In this way, droplet size is independent of the exact natures of the fluids or of any contamination they might suffer, and it depends to a very small extent only on the viscosity of the fluids.

Finally, the size of the droplets is also unaffected by the shape of the walls situated at a distance from the outlet of the microchannel, thus enabling various chamber shapes to be used.

By way of example, the chamber used has a substantially rectangular section of height that extends between the two diverging opposite walls and of length that is long relative to its height.

By way of example, its length may be greater than ten times its height.

Naturally, the chamber may present other shapes. In particular, the walls of the chamber may diverge in more than one direction. By way of example, the chamber may be spherical or egg-shaped.

In preferred manner, the height of the chamber at the outlet from the microchannel is less than the diameter of the droplets to be formed.

In a variant, one of the walls of the chamber includes a step, a concave portion, or a convex portion at the outlet of the microchannel.

These variations in the shape of the inlet of the chamber serve to control the size and the travel speed of the droplets. It is thus the presence of a step that enables smaller droplets to be formed, while a concave portion enables the travel speed of the droplets after they have formed to be reduced, and a convex portion enables droplet size to be better calibrated.

In a first embodiment, the flow rate of the first fluid in the chamber is substantially zero.

In a variant embodiment, the flow rate of the first fluid in the chamber is adjusted to a determined value.

By way of example, the divergence of the two opposite walls of the chamber corresponds to a slope of one of the walls relative to the other lying in the range 1% to 4%, approximately.

Naturally, these values are given purely by way of example, and the slope may have a value that is infinitesimal or a value of 100%, i.e. corresponding to a wall that is vertical relative to a horizontal wall.

According to another characteristic of the invention, the device includes means for locally modifying the surface tension of the second fluid.

This makes it possible in particular to adjust the size of the droplets that are produced compared with the size they would have without the surface tension being modified.

In an embodiment of the invention, the means for modifying the surface tension of the second fluid comprise means for heating the second fluid, e.g. using a locally-applied laser beam or electrodes incorporated in the microfluidic circuit or by using other temperature control means.

If the zone situated directly upstream from the outlet of the microchannel is heated, the surface tension tending to retain the second fluid in the microchannel decreases and the force needed to pull a droplet of the second fluid away from the microchannel is smaller. Directly heating the outlet from upstream therefore tends to reduce the size of the droplets.

Conversely, if the zone situated directly downstream from the outlet of the microchannel is heated, then the surface tension tending to extract the second fluid from the microchannel is decreased. Heating directly downstream from the outlet therefore tends to increase the size of the droplets.

In general, heating produces the same effects as increasing the section of the outlet of the microchannel, with respect to droplet formation and detachment.

According to another characteristic of the invention, the device includes a plurality of microchannels leading into the chamber. The microchannels may contain fluids that are independent, or they may be in the form of ramifications stemming from a common channel situated upstream from the microchannels.

In a first variant, the microchannels are substantially mutually parallel and lead into a common side of the chamber.

In a second variant, the chamber is annular in shape, the microchannels being arranged in a star configuration and leading into the inner periphery of the chamber.

In a particular embodiment of the invention, the device comprises a body made up of two portions, the microchannel and the chamber each having one wall defined by one of these two portions and another wall defined by the other one of these two portions.

In this way, it is possible to cause the properties of the droplets (size, speed, . . . ) to vary merely by changing one or the other of the two above-mentioned portions.

This also makes it possible to have a microchannel of small height and thus to form droplets that are very small (e.g. less than 10 micrometers ($\mu$m), for example), compared with using a body made as a single piece.

The invention also provides a method of forming droplets of a second fluid in a first fluid contained in a microfluidic circuit, the method being characterized in that it consists in bringing the second fluid to the inlet of a chamber containing the first fluid, the inlet of the chamber comprising two opposite walls that diverge inside the chamber, and in urging the second fluid into the inlet of the chamber to form a droplet of the second fluid inside the chamber, the droplet enlarging progressively between the two opposite diverging walls of the chamber until its upstream end becomes detached from the delivery of the second fluid.

In preferred manner, the method consists in adjusting the size of the droplets of the second fluid by adjusting the feed section of the second fluid at the inlet of the chamber and by adjusting the divergence of said opposite walls of the chamber, and/or by modifying the surface tension by laser beam heating or by heating using electrodes integrated in the microfluidic circuit or by other temperature control means.

BRIEF DESCRIPTION OF THE DRAWINGS

The invention can be better understood and other details, characteristics, and advantages of the invention appear on reading the following description made by way of non-limiting example and with reference to the accompanying drawings, in which.

DETAILED DESCRIPTION

Figure 1:
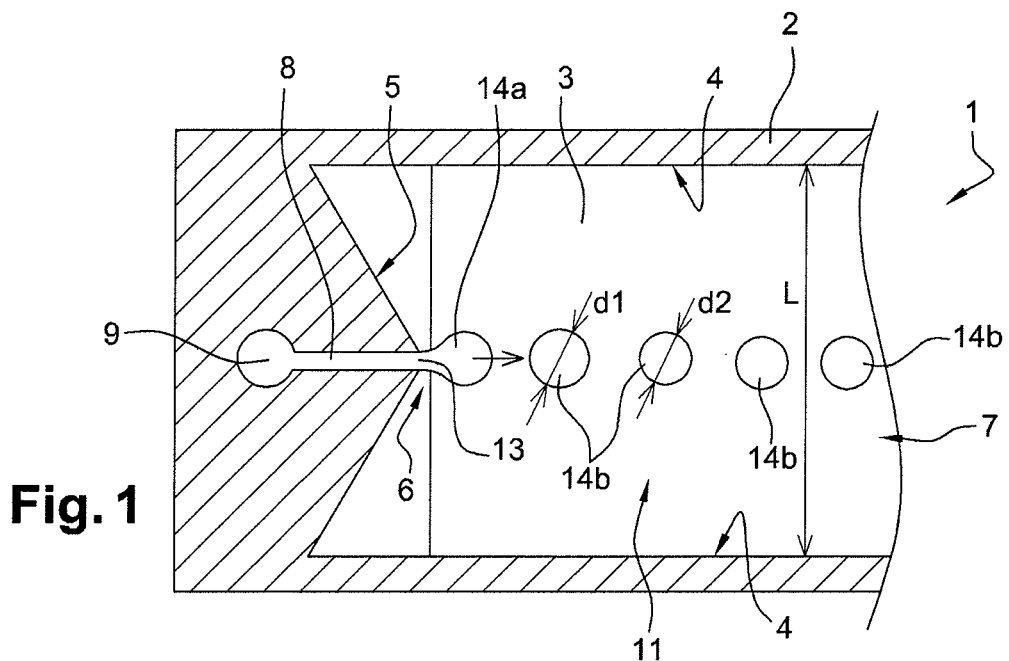
FIG. 1 is a longitudinal section view of the device of the invention.
Figure 2:
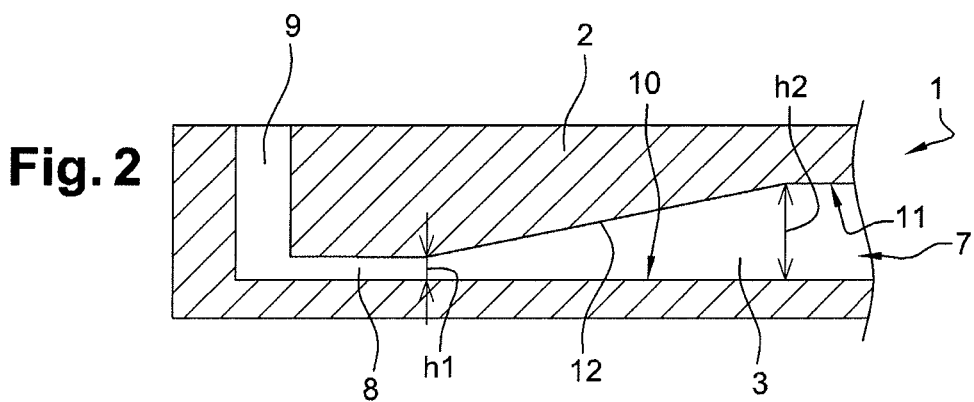
FIG. 2 is a cross-section view of the device in which the droplets formed are not shown.

FIGS. 1 and 2 show a device 1 for forming droplets in a microfluidic circuit, the device comprising a body 2 having formed therein a chamber 3 that is defined by two parallel and opposite side walls 4 and by two opposite longitudinal walls 10 and 11. The width L of the chamber 3, i.e. the distance between the two side walls 4 is of the order of 2 millimeters (mm) for example. The chamber 3 also has an end wall 5 in the form of a point 6 directed towards an opposite end 7 of the chamber 3.

The body 2 also has a microchannel 8 with one end connected to a connection orifice 9, in particular for connecting a syringe or a pipette, and with its other end leading into the chamber 3 via the point 6 of the end wall 5.

The bottom longitudinal wall 10 of the chamber is a plane wall and the top longitudinal wall 11 presents a sloping portion 12 that moves progressively away from the bottom longitudinal wall 10 on going towards the opposite end 7 of the chamber 3. By way of example, the divergence between the two opposite walls 10 and 11 of the chamber 3 may correspond, to one of the walls sloping relative to the other at a slope lying in the range 1% to 4% approximately.

In this way, the section of the chamber 3 increases progressively from the zone into which the microchannel 8 leads on going towards the opposite end 7. The minimum height h1 of the chamber 3, i.e. the height of the chamber 3 at the outlet 13 of the microchannel 8 is of the order of 10 μm to 100 μm, and the maximum height h2 of the chamber 3, i.e. the height of the chamber 3 at its open end 7 is of the order of 20 μm to 1000 μm.

The device 1 may be associated with means for locally modifying the surface tension of the second fluid, which means comprise means for heating the second fluid, e.g. by using electrodes integrated in the microcircuit or by using external temperature control. Surface tension decreases linearly with temperature so that, for a constant area, it is possible to change the surface energy (equal to the product of the total area multiplied by the surface tension) by heating by using electrodes, in order to produce the same effects as increasing the section of the outlet of the microchannel 8, with a decrease in temperature gradient at the outlet.

Figure 9:
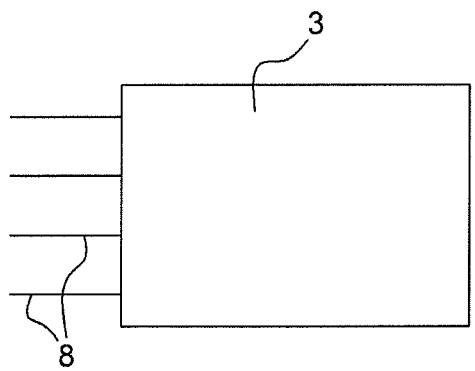
FIG. 9 is a diagrammatic view of a variant embodiment in which a plurality of microchannels are arranged in parallel and lead into the chamber.

A variant embodiment of the invention is shown in FIG. 9. In this embodiment, the chamber 3 is of rectangular shape, and it is connected to a plurality of substantially parallel microchannels 8 all leading to a common side of the chamber 3.

Figure 10:
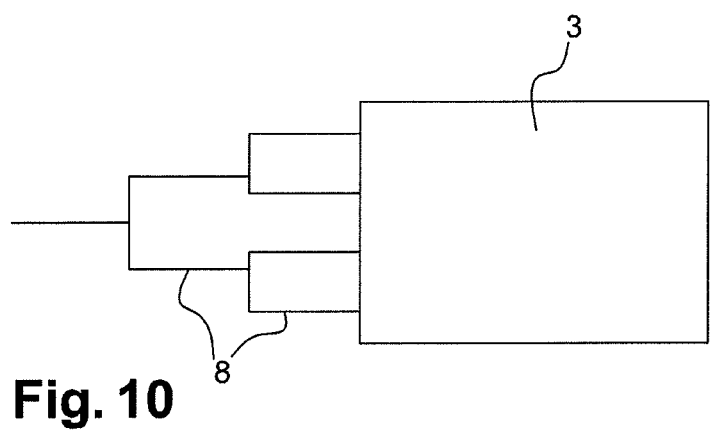
FIG. 10 is a diagrammatic view of another variant embodiment in which the microchannels form ramifications leading into the chamber.

Another variant is shown in FIG. 10 in which the device has an array of microchannels 8 constituting ramifications, each ramification coming from a single original channel located upstream. The various ramifications lead into a common side of the chamber 3.

Figure 11:
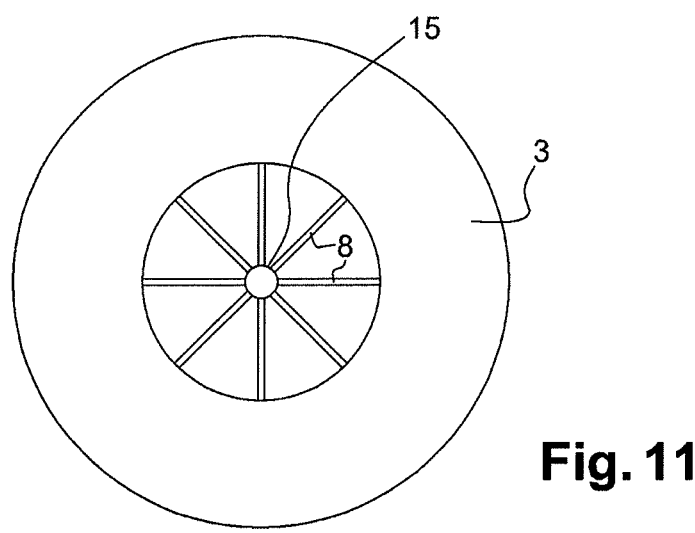
FIG. 11 is a diagrammatic view of another variant embodiment in which the chamber is annular, the microchannels being arranged in a star configuration.

A final variant is shown in FIG. 11. In this variant, the channel 3 is annular in shape and the device has a plurality of microchannels 8 arranged in a star configuration, the microchannels extending radially from a common source 15 and leading into the inner periphery of the chamber 3.

These variant embodiments enable a plurality of streams of droplets to be formed simultaneously within a single chamber. This is particularly useful when it is desired to produce populations of droplets, e.g. containing different ingredients. Depending on requirements, the droplets as formed in this way may be manipulated or extracted from the device in the form of a foam or an emulsion.

The operation of this droplet-forming device is described in detail below.

The chamber 3 is filled with a first fluid, e.g. oil. A syringe containing a second fluid, e.g. water, is then connected to the connection orifice 9 and the water is injected into the microchannel 8 until it reaches the outlet 13 of the microchannel 8.

As mentioned above, the water situated at the outlet 13 of the microchannel 8 is subjected to two opposing forces due to surface tension. A first tension is due to a surface energy gradient tending to extract the water from the microchannel 8, forming a finger 14a that projects into the chamber 3 and that is attached to the water contained in the microchannel 8.

A second force, opposite to the first and corresponding to capillary force, tends to keep the finger 14a attached to the water contained in the microchannel 8.

The finger 14a detaches when the first force becomes greater than the second force. For a given shape of the microchannel 8 and of the chamber 3, this first force is a function of the volume of the finger 14a. Thus, in operation, the volume of the finger 14a increases progressively until the first force becomes greater than the second force and the finger becomes detached so as to form a droplet 14b.

The dimensions of the microchannel 8 and the enlarging of the section of the chamber 3 are determined in such a manner as to obtain a droplet 14 of determined size. In particular, the height h1 of the chamber 3 at the outlet of the microchannel must be less than the diameter of the droplets 14 that are to be formed.

Water droplets 14b are thus formed in succession in the chamber, providing water is delivered to the outlet 13 of the microchannel 8.

Depending on requirements, a flow of oil may be imposed in the chamber 3.

The droplets 14b formed at the outlet 13 of the microchannel 8 are transported naturally towards the opposite end 7 of the chamber 3 because of the increasing flow section available to them in the chamber. As mentioned above, a droplet 14b situated in a zone of small section, where it takes up a flattened shape, is naturally attracted to a zone of greater section in which it can occupy a shape that is more spherical and thus less stressed. As can be seen in FIG. 1, droplets 14b close to the point 6 present an apparent diameter d1 that is greater than the apparent diameter d2 of droplets 14b close to the second end 7 as a result of being flattened between the walls 10 and 12.

Figure 3:
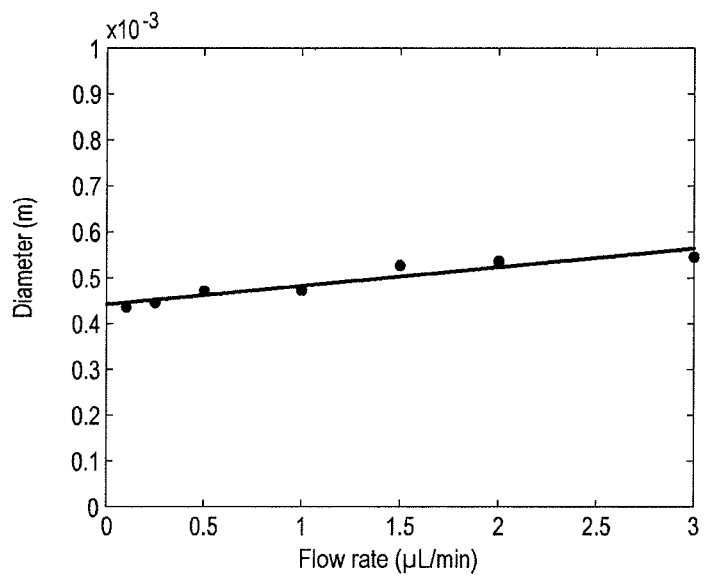
FIG. 3 is a graph plotting the size of the droplets produced as a function of the flow rate of the second fluid.

FIG. 3 is a graph plotting variation in the diameter of droplets 14b as measured at a given position as a function of the flow rate of water arriving via the microchannel 8. It should be observed that this variation is practically zero even for very great variation of the applied flow rate, thereby demonstrating that the invention makes it possible to obtain droplets 14 of calibrated size regardless of operating conditions, thereby making such a droplet-forming device simpler to operate. In the example shown in FIG. 3, the size of the droplets 14b is of the order of a few hundreds of micrometers, however reducing the dimensions of the device 1 makes it possible to obtain droplets 14 having a size of a few hundreds of nanometers, without significantly modifying its operation.

The operation of the device is, in particular, independent of the natures of the fluids (gas or liquid) and of the value of the surface tension.

Figure 4:
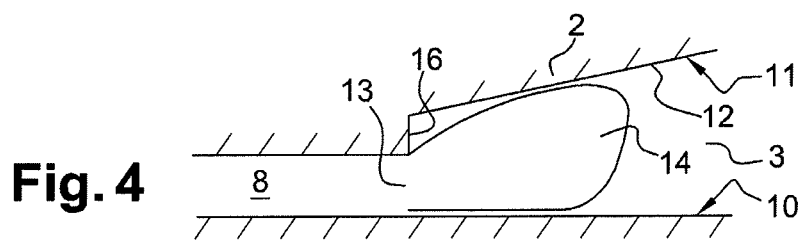
FIGS. 4 to 6 are diagrammatic cross-section views of the device showing three variant embodiments of the invention.

In a variant embodiment shown in FIG. 4, the outlet 13 of the microchannel 8 into the chamber 3 includes a step 16, i.e. a sudden change in the section of the microchannel. This step 16 is formed in the top wall 11. The top wall thus has a portion 16 that is perpendicular to the microchannel and forms the step, and that is extended by a sloping portion 12 forming an angle relative to the bottom wall 10, in the same manner as described above. Such a step 16 may be used to form droplets of smaller size for a given slope.

Figure 5:
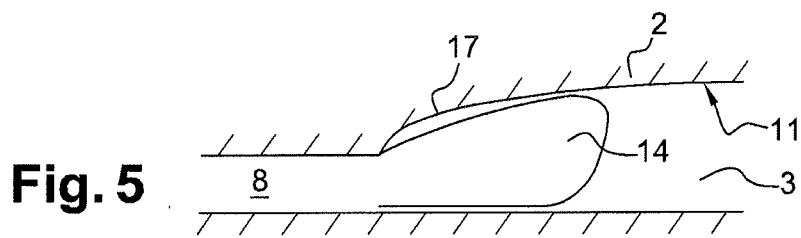

FIG. 5 shows another variant embodiment in which the step is replaced by a concave connection zone 17 of the top wall 11, which zone connects the outlet 13 of the microchannel 8 to the sloping portion 12.

This makes it possible to form droplets or bubbles that travel at a speed that is slower than that of the droplets or bubbles that are formed with the device of FIG. 2.

Figure 6:
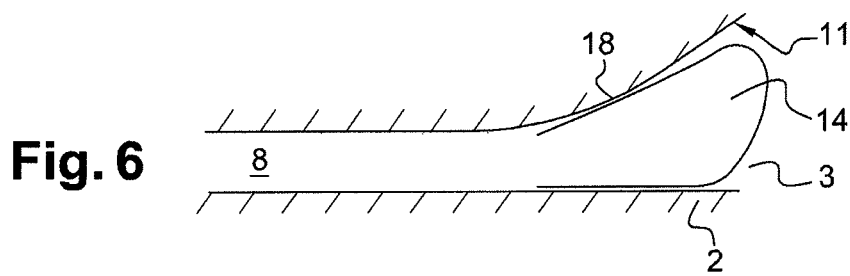

FIG. 6 shows yet another variant embodiment in which the connection zone 18 of the top wall 11 is convex. This makes it possible to form droplets of a size that is better calibrated.

Figure 7:
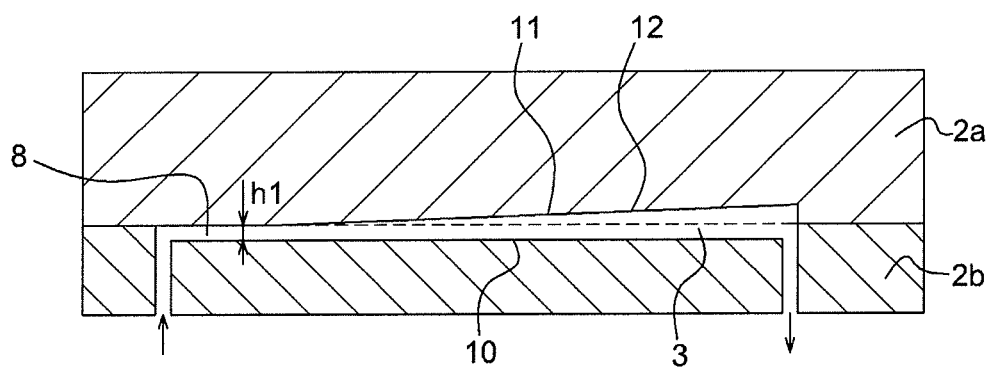
FIG. 7 is a view corresponding to FIG. 2, showing a device made up of two portions.

FIG. 7 shows an embodiment of the invention similar to that of FIG. 2 and in which the body 2 is made up of two portions, respectively a top portion 2a and a bottom portion 2b. The sloping portion 12 of the top wall 11 of the chamber 3 is made in the top portion 2a, e.g. by milling or by any other appropriate method. The bottom portion 2b includes the microchannels 8, e.g. made by photolithography, by plastic forming, or by any other suitable method.

In this way, it is possible to vary the properties of the droplets (size, speed, . . . ) merely by changing one or other of the portions 2a, 2b.

This also makes it possible to have a microchannel of small height and thus to form droplets that are very small (e.g. less than 10 μm), compared with a single-piece body.

The materials used for the portions 2a and 2b may be different or they may be the same. Furthermore, the portions 2a and 2b may be stuck together in non-separable manner so as to form a device for producing droplets of the same size. Conversely, they may be fastened together in separable manner so as to enable the size of the droplets to be changed by replacing one or other of the portions.

Figure 8:
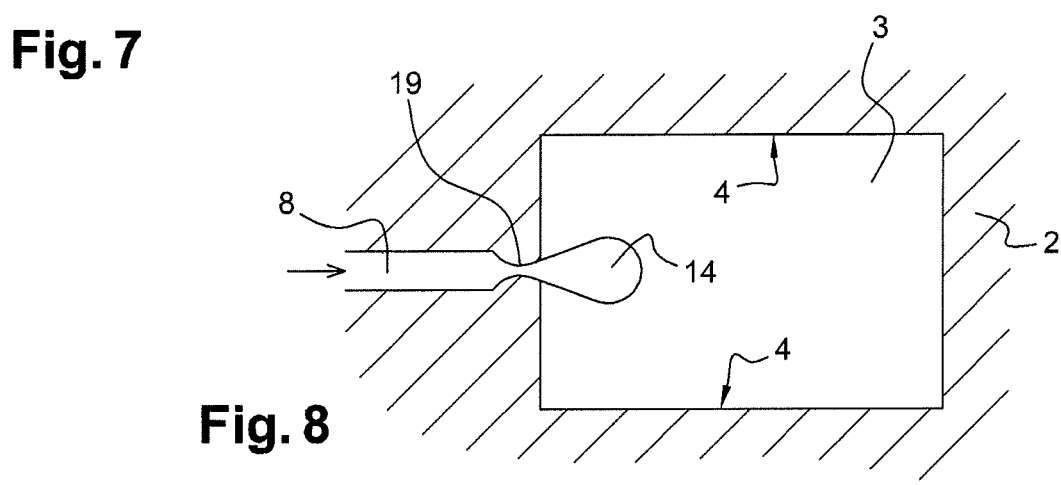
FIG. 8 is a longitudinal section view of the device in a variant embodiment of the invention.

FIG. 8 shows an embodiment in which the microchannel includes a zone 19 of smaller width, i.e. a constriction. In a variant, this zone could be a localized enlargement (not shown). In this way, the droplet 14 becomes detached from the remainder of the fluid contained in the microchannel 8, in a manner that is selective and controlled, at the location of the constriction or the enlargement, thereby making it possible to obtain better control over the size of the droplets produced.

The invention claimed is:

1. A method of forming a droplet of a second fluid in a first fluid contained in a microfluidic circuit, the method consisting in;

bringing the second fluid to an inlet of a chamber containing the first fluid, the inlet of the chamber comprising two opposite walls of the chamber that diverge inside the chamber, urging the second fluid into the inlet of the chamber to form a finger of the second fluid projecting into the chamber and attached to the second fluid, the finger enlarging progressively between the two opposite diverging walls of the chamber, the finger being flattened between said opposite diverging walls, until its upstream end becomes detached from the delivery of the second fluid, to form the droplet, wherein said microfluidic circuit does not comprise any additional channel conveying a flow of said first fluid for shearing the second fluid and forming said droplet.

2. A method according to claim 1, comprising a step of consisting in adjusting the size of the droplets of the second fluid by adjusting a feed section of the second fluid at the inlet of the chamber and the divergence of said opposite walls of the chamber.

3. A method according to claim 1, comprising a step of modifying the surface tension of said second fluid.

4. A method according to claim 1, wherein only said second fluid is urged into the inlet of the chamber.

5. A method according to claim 1, wherein the chamber has a zone of small section, near said inlet of the chamber, in which the droplet takes up a flattened shape, and a zone of greater section, distant from the inlet of the chamber, to which said droplet is naturally attracted and in which said droplet occupies a shape that is more spherical and thus less stressed.

6. A method according to claim 1, wherein the flow rate of the first fluid in the chamber is adjusted to a determined value.

7. A method according to claim 1, wherein the height of the chamber at the inlet is less than the diameter of the droplets to be formed.

8. A method of forming a droplet of a second fluid in a first fluid contained in a microfluidic circuit, the method consisting in:

bringing the second fluid to an inlet of a chamber containing the first fluid, the inlet of the chamber comprising two opposite walls of the chamber that diverge inside the chamber, and urging the second fluid into the inlet of the chamber to form a finger of said second fluid projecting into the chamber, the finger enlarging progressively between the two opposite diverging walls of the chamber, the finger being flattened between said opposite diverging walls, until its upstream end becomes detached from the delivery of the second fluid, to form the droplet, wherein the flow rate of the first fluid in the chamber is substantially zero.

9. A method according to claim 8, comprising a step of adjusting a feed section of the second fluid at the inlet of the chamber and the divergence of said opposite walls of the chamber.

10. A method according to claim 8, comprising a step of modifying the surface tension of said second fluid.

11. A method according to claim 8, wherein only said second fluid is urged into the inlet of the chamber.

12. A method according to claim 8, wherein the chamber has a zone of small section, near said inlet of the chamber, in which the droplet takes up a flattened shape, and a zone of greater section, distant from the inlet of the chamber, to which said droplet is naturally attracted and in which said droplet occupies a shape that is more spherical and thus less stressed.

13. A method according to claim 8, wherein the height of the chamber at the inlet is less than the diameter of the droplets to be formed.

14. A method of forming a droplet of a second fluid in a first fluid contained in a microfluidic circuit, the method consisting in:

bringing the second fluid to an inlet of a chamber containing the first fluid through a microchannel, the inlet of the chamber comprising two opposite walls that diverge inside the chamber, and in urging the second fluid into the inlet of the chamber to form a finger of said second fluid projecting into the chamber and attached to the second fluid contained in the microchannel, said finger of second fluid being subjected to two opposing forces due to surface tension:

a first force being due to a surface energy gradient tending to extract the second fluid from the microchannel, a second force corresponding to capillary force being opposite to said first force and tending to keep the finger attached to the second fluid contained in the microchannel, the finger enlarging progressively between the two opposite diverging walls of the chamber, the finger being flattened between said opposite diverging walls, until its upstream end becomes detached from the second fluid contained in the microchannel to form a droplet, when the first force become greater than the second force.

15. A method according to claim 14, comprising a step of adjusting a feed section of the second fluid at the inlet of the chamber and the divergence of said opposite walls of the chamber.

16. A method according to claim 14, comprising a step of modifying the surface tension of said second fluid.

17. A method according to claim 14, wherein only said second fluid is urged into the inlet of the chamber.

18. A method according to claim 14, wherein the chamber has a zone of small section, near said inlet of the chamber, in which the droplet takes up a flattened shape, and a zone of greater section, distant from the inlet of the chamber, to which said droplet is naturally attracted and in which said droplet occupies a shape that is more spherical and thus less stressed.

19. A method according to claim 14, wherein the flow rate of the first fluid in the chamber is adjusted to a determined value.

20. A method according to claim 14, wherein the height of the chamber at the inlet is less than the diameter of the droplets to be formed.

21. A microfluidic circuit for forming droplets of a second fluid in a first fluid, wherein the micro fluidic circuit comprises:

a chamber configured to contain a first fluid, said chamber comprising two opposite longitudinal walls that diverge in said chamber relative to each other in at least one given direction, and a microchannel for containing a second fluid that leads into a zone of said chamber that is upstream relative to the given direction, through an inlet, wherein the inlet into the chamber includes an increase in the flow section for the second fluid in two directions perpendicular to said given direction, wherein said micro fluidic circuit does not comprise any additional channel configured for conveying a flow of said first fluid into said microchannel or said zone of said chamber, and configured for shearing the second fluid into droplets.

22. A microfluidic circuit according to claim 21, wherein said chamber is of substantially rectangular section, the height of said section being defined between the two longitudinal opposite diverging walls, the length of said chamber being long relative to the height of said section.

23. A microfluidic circuit according to claim 21, wherein one of the walls of the chamber includes a step, a concave portion, or a convex portion at a outlet of the microchannel in the chamber.

24. A microfluidic circuit according to claim 21, wherein the divergence of the two opposite longitudinal walls of the chamber corresponds to a slope of one the longitudinal walls relative to the other lying in the range from 1% to 4%.

25. A microfluidic circuit according to claim 21, wherein said microfluidic circuit includes a plurality of microchannels leading into the chamber.

26. A microfluidic circuit according to claim 25 wherein said microchannels are substantially mutually parallel and lead into a common side of said chamber.

27. A microfluidic circuit according to claim 25, wherein the chamber is annular in shape, the microchannels being arranged in a star configuration and leading into the inner periphery of the chamber.

28. A microfluidic circuit according to claim 21, wherein the microfluidic circuit comprises a body made up of two portions, the microchannel and the chamber each having one wall defined by one of the portions and another wall defined by the other portion.

* * * * *